United States Patent

Lacefield et al.

[11] 4,021,553
[45] * May 3, 1977

[54] 5,6-DIARYL-1,2,4-TRIAZINES AS TOPICALLY-ACTIVE ANTI-INFLAMMATORY AGENTS

[75] Inventors: William B. Lacefield, Indianapolis; Peter P. K. Ho, Carmel, both of Ind.

[73] Assignee: Eli Lilly and Company, Indianapolis, Ind.

[*] Notice: The portion of the term of this patent subsequent to Apr. 19, 1994, has been disclaimed.

[22] Filed: Mar. 10, 1976

[21] Appl. No.: 665,590

[52] U.S. Cl. ............................................... 424/249
[51] Int. Cl.² ............................................... A61K 31/53
[58] Field of Search ............ 424/249; 260/248 AS

[56] References Cited

UNITED STATES PATENTS 3,211,729 10/1965 Siegrist et al. ............... 424/249
3,644,358 2/1972 Roffey et al. ............... 424/249

OTHER PUBLICATIONS

Chem. Abst., 46: 514b (1952).
Chem. Abst., 47: 11209e (1953).
Chem. Abst., 51: 13875i (1957).
Chem. Abst., 51: 15532d (1957).
Chem. Abst.., 75: 129,773g (1971).
H. Neunhoeffer et al., *Justus Liebigs Ann. Chem.*, 760, 88 (1972).
H. Neunhoeffer et al., *Chem. Ber.* 101, 3952 (1968).

Primary Examiner—Stanley J. Friedman
Attorney, Agent, or Firm—William E. Maycock; Everet F. Smith

[57] ABSTRACT

A method of treating inflammation which utilizes topically-active 5,6-diaryl-1,2,4-triazines having the formula,

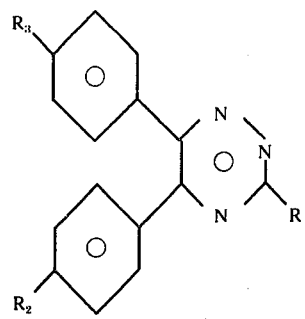

wherein R is hydrogen or $-(X)_nR_1$, in which X is either O or S, $n$ is an integer which is either 0 or 1, and $R_1$ is $C_1-C_8$ alkyl, $C_7-C_8$ aralkyl, $C_3-C_8$ cycloalkyl, or $C_4-C_8$ (cycloalkyl)alkyl; and $R_2$ and $R_3$ independently are $C_1-C_3$ alkoxy or di($C_1-C_3$ alkyl)amino; and the pharmaceutically-acceptable acid addition salts of basic members thereof.

10 Claims, No Drawings

5,6-DIARYL-1,2,4-TRIAZINES AS TOPICALLY-ACTIVE ANTI-INFLAMMATORY AGENTS

BACKGROUND OF THE INVENTION

This invention relates to anti-inflammatory 5,6-diaryl-1,2,4-triazines. More particularly, this invention relates to a method of treating inflammation with topically-active anti-inflammatory 5,6-diaryl-1,2,4-triazines.

Inflammation is an essentially protective and normal response to injury, although the etiology and pathogenesis of many inflammatory conditions remain obscure. In general, anti-inflammatory agents are employed primarily to relieve the symptoms of inflammation. In such symptomatic therapy, topically-applied anti-inflammatory agents present special problems. Inflammatory conditions calling for the topical application of an anti-inflammatory agent are almost exclusively treated with steroids. Topically-applied steroids, however, may carry considerable systemic toxicity. Thus, the need continues for safer, better tolerated topically-active anti-inflammatory agents.

SUMMARY OF THE INVENTION

In accordance with the present invention, a method of treating inflammation in a warm-blooded mammal is provided which comprises topically administering to such mammal an effective amount of a compound of the formula,

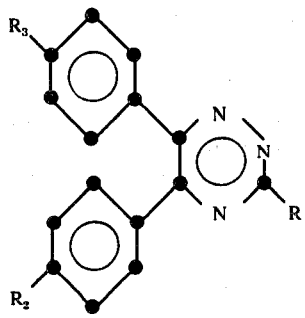

wherein R is hydrogen or $-(X)_nR_1$, in which X is either O or S, $n$ is an integer which is either 0 or 1, and $R_1$ is $C_1-C_8$ alkyl, $C_7-C_8$ aralkyl, $C_3-C_8$ cycloalkyl, or $C_4-C_8$ (cycloalkyl)alkyl; and $R_2$ and $R_3$ independently are $C_1-C_3$ alkoxy or di($C_1-C_3$ alkyl) amino; and the pharmaceutically-acceptable acid addition salts of basic members thereof.

As used herein, an effective amount means an amount sufficient to at least in part ameliorate the inflammatory condition under treatment. The relief afforded thereby can be observed as a reduction in the intensity of the inflammation, a reduction in the timer period during which the inflammatory condition persists, or both, and in instances where pretreatment is possible, a delay in the appearance of the inflammatory condition also can be observed.

The compounds employed in the present invention are especially useful as topically-active anti-inflammatory agents in warm-blooded mammals, such as guinea pigs, mice, rats, dogs, monkeys, humans, and the like.

DETAILED DESCRIPTION OF THE INVENTION

The term $C_1-C_8$ alkyl includes methyl, ethyl, propyl, isopropyl, butyl, isobutyl, sec-butyl, tert-butyl, pentyl, isopentyl, 1-methylbutyl, 1-ethylpropyl, neopentyl, tert-pentyl, 1,2-dimethylpropyl, hexyl, isohexyl, 2-ethylbutyl, 1-ethyl-1-methylpropyl, heptyl, 2-ethyl-1-methylbutyl, 2,4-dimethylpentyl, octyl, 2-ethylhexyl, 1,1-diethylbutyl, and the like.

The term $C_7-C_8$ aralkyl includes benzyl, 2-phenylethyl, p-methylbenzyl, m-methylbenzyl, o-methylbenzyl, and the like.

The term $C_3-C_8$ cycloalkyl includes cyclopropyl, 2-butylcyclopropyl, cyclobutyl, 2-ethyl-3-methylcyclobutyl, cyclopentyl, 3-isopropylcyclopentyl, cyclohexyl, 1-methylcyclohexyl, 2,5-dimethylcyclohexyl, cycloheptyl, 5-methylcycloheptyl, cyclooctyl, and the like.

The term $C_4-C_8$ (cycloalkyl)alkyl includes cyclopropylmethyl, 3-cyclopropyl-2-methylbutyl, 3-(2-methylcyclobutyl)propyl, 2-cyclopentylethyl, 2-methylcyclohexylmethyl, cycloheptylmethyl, and the like.

The term $C_1-C_3$ alkoxy includes methoxy, ethoxy, propoxy, and isopropoxy. The term $C_1-C_3$ alkyl includes methyl, ethyl, propyl, and isopropyl.

Illustrative of the triazine compounds which are employed in the present invention are the following:
5,6-bis(4-methoxyphenyl)-1,2,4-triazine,
5,6-bis(4-ethoxyphenyl)-1,2,4-triazine,
5,6-bis(4-dimethylaminophenyl)-1,2,4-triazine,
5,6-bis(4-dipropylaminophenyl)-1,2,4-triazine,
5-(4-diethylaminophenyl)-6-(4-methoxyphenyl)-1,2,4-triazine,
5,6-bis(4-methoxyphenyl)-3-methyl-1,2,4-triazine,
3-ethyl-5,6-bis(4-methoxyphenyl)-1,2,4-triazine,
5,6-bis(4-methoxyphenyl)-3-propyl-1,2,4-triazine,
3-isopropyl-5,6-bis(4-methoxyphenyl)-1,2,4-triazine,
3-tert-butyl-5,6-bis(4-methoxyphenyl)-1,2,4-triazine,
3-(1,2-dimethylpropyl)-5,6-bis(4-methoxyphenyl)-1,2,4-triazine,
3-heptyl-5,6-bis(4-methoxyphenyl)-1,2,4-triazine,
5,6-bis(4-ethoxyphenyl)-3-methyl-1,2,4-triazine,
5,6-bis(4-ethoxyphenyl)-3-ethyl-1,2,4-triazine,
5,6-bis(4-ethoxyphenyl)-3-propyl-1,2,4-triazine,
5,6-bis(4-ethoxyphenyl)-3-isopropyl-1,2,4-tri-azine.
5,6-bis(4-ethoxyphenyl)-3-hexyl-1,2,4-triazine,
3-ethyl-5,6-bis(4-propoxyphenyl)-1,2,4-triazine,
3-(1-methylbutyl)-5,6-bis(4-propoxyphenyl)-1,2,4-triazine,
3-neoheptyl-5,6-bis(4-propoxyphenyl-1,2,4-triazine,
5,6-bis(4-isopropoxyphenyl)-3-methyl-1,2,4-triazine,
3-sec-butyl-5,6-bis(4-isopropoxyphenyl)-1,2,4-triazine,
5,6-bis(4-isopropoxyphenyl)-3-octyl-1,2,4-triazine,
5-(4-methoxyphenyl)-3-methyl-6-(4-propoxyphenyl)-1,2,4-triazine,
6-(4-ethoxyphenyl)-5-(4-isopropoxyphenyl)-3-(2,3,4-trimethylpentyl)-1,2,4-triazine,
5,6-bis(4-dimethylaminophenyl)-3-methyl-1,2,4-triazine,
5,6-bis(4-dimethylaminophenyl)-3-ethyl-1,2,4-triazine,
5,6-bis(4-dimethylaminophenyl)-3-propyl-1,2,4-triazine, 5,6-bis(4-dimethylaminophenyl)-3-isopropyl-1,2,4-triazine,
5,6-bis(4-dimethylaminophenyl)-3-isopentyl-1,2,4-triazine,
5,6-bis(4-dimethylaminophenyl)-3-(2-ethylhexyl)-1,2,4-triazine,
5,6-bis(4-diethylaminophenyl)-3-methyl-1,2,4-triazine,
5,6-bis(4-diethylaminophenyl)-3-ethyl-1,2,4-triazine,
5,6-bis(4-diethylaminophenyl)-3-propyl-1,2,4-triazine,
5,6-bis(4-diethylaminophenyl)-3-isopropyl-1,2,4-triazine,
5,6-bis(4-diethylaminophenyl)-3-(2,2,3-trimethylbutyl)-1,2,4-triazine,
5,6-bis(4-dipropylaminophenyl)-3-methyl-1,2,4-triazine,
3-sec-butyl-5,6-bis(4dipropylaminophenyl)-1,2,4-triazine,
5,6-bis(4-dipropylaminophenyl)-3-(2-ethylbutyl)-1,2,4-triazine,
5,6-bis(4-diisopropylaminophenyl)-3-ethyl-1,2,4-triazine,
5,6-bis(4-diisopropylaminophenyl)-3-tert-pentyl-1,2,4-triazine,
5,6-bis(4-diisopropylaminophenyl)-3-(2,2,4-trimethylpentyl)-1,2,4-triazine,
6-(4-diisopropylaminophenyl)-5-(4-dimethylaminophenyl)-3-neoheptyl-1,2,4-triazine,
5-(4-diisopropylaminophenyl)-6-(4-ethoxyphenyl)-3-methyl-1,2,4-triazine,
3-benzyl-5,6-bis(4-methoxyphenyl)-1,2,4-triazine,
5,6-bis(4-methoxyphenyl)-3-(m-methylbenzyl)-1,2,4-triazine,
5,6-bis(4-ethoxyphenyl)-3-(2-phenylethyl)-1,2,4-triazine.
3-(1-phenylethyl)-5,6-bis(4-propoxyphenyl)-1,2,4-triazine,
5,6-bis(4-isopropoxyphenyl)-3-(o-methylbenzyl)-1,2,4-triazine,
3-benzyl-5-(4-methoxyphenyl)-6-(4-propoxyphenyl)-1,2,4-triazine,
5,6-bis(4-diethylaminophenyl)-3-p-methylbenzyl-1,2,4-triazine,
5-(4-diethylaminophenyl)-6-(4-diisopropylaminophenyl-3-(2-phenylethyl)-1,2,4-triazine,
3-benzyl-6-(4-diethylaminophenyl)-5-(4-ethoxyphenyl)-1,2,4-triazine,
3-cyclopropyl-5,6-bis(4-methoxyphenyl)-1,2,4-triazine,
3-cyclopentyl-5,6-bis(4-propoxyphenyl)-1,2,4-triazine,
3-cyclobutyl-5-(4-ethoxyphenyl)-6-(4-methoxyphenyl)-1,2,4-triazine,
3-cyclooctyl-5,6-bis(4-dimethylaminophenyl)-1,2,4-triazine,
5,6-bis(4-dipropylaminophenyl)-3-(2-ethylcyclopropyl)-1,2,4-triazine,
5-(4-diethylaminophenyl)-6-(4-dipropylamnophenyl)-3-(2-ethylcyclobutyl)-1,2,4-triazine,
3-cycloheptyl-6-(4-dipropylaminophenyl)-5-(4-methoxyphenyl)-1,2,4-triazine,
3-(2-cyclohexylethyl)-5,6-bis(4-ethoxyphenyl)-1,2,4-triazine,
3-cyclobutylmethyl-5,6-bis(4-isopropoxyphenyl)-1,2,4-triazine,
5-(4-ethoxyphenyl)-6-(4-isopropoxyphenyl)-3-(2-methylcyclohexylmethyl)-1,2,4-triazine,
3-cyclopropylmethyl-5,6-bis(4-diethylaminophenyl)-1,2,4-triazine,
5,6-bis(4-dipropylaminophenyl)-3-[2-(2-methylcyclobutyl)ethyl]-1,2,4-triazine,
3-cycloheptylmethyl-5,6-bis(4-diisopropylaminophenyl)-1,2,4-triazine,
3-(1-cyclohexylethyl)-5-(4-diethylaminophenyl)-6-(4-dimethylaminophenyl)-1,2,4-triazine,
3-cyclopentylmethyl-5-(4-diethylaminophenyl)-6-(4-ethoxyphenyl)-1,2,4-triazine,
3-methoxy-5,6-bis(4-methoxyphenyl)-1,2,4-triazine,
3-ethoxy-5,6-bis(4-methoxyphenyl)-1,2,4-triazine,
5,6-bis(4-methoxyphenyl)-3-propoxy-1,2,4-triazine,
3-isopropoxy-5,6-bis(4-methoxyphenyl)-1,2,4-triazine,
3-hexyloxy-5,6-bis(4-methoxyphenyl)-1,2,4-triazine,
3-(1,2-diethylbutoxy)-5,6-bis(4-methoxyphenyl)-1,2,4-triazine,
5,6-bis(4-ethoxyphenyl)-3-methoxy-1,2,4-triazine,
3-ethoxy-5,6-bis(4-ethoxyphenyl)-1,2,4-triazine,
5,6-bis(4-ethoxyphenyl)-3-propoxy-1,2,4-triazine,
5,6-bis(4-ethoxyphenyl)-3-isopropoxy-1,2,4-triazine,
5,6-bis(4-ethoxyphenyl)-3-neopentyloxy-1,2,4-triazine,
5,6-bis(4-ethoxyphenyl)-3-(1-ethyl-2-methylbutoxy)-1,2,4-triazine,
3-methoxy-5,6-bis(4-propoxyphenyl)-1,2,4-triazine,
3-ethoxy-5,6-bis(4-propoxyphenyl)-1,2,4-triazine,
3-propoxy-5,6-bis(4-propoxyphenyl)-1,2,4-triazine,
3-hexyloxy-5,6-bis(4-propoxyphenyl)-1,2,4-triazine,
3-ethoxy-5,6-bis(4-isopropoxyphenyl)-1,2,4-triazine,
3-(1-ethylbutoxy)-5,6-bis(4-isopropoxyphenyl)-1,2,4-triazine,
3-(2-ethylhexyloxy-5,6-bis(4-isopropoxyphenyl)-1,2,4-triazine,
6-(4-ethoxyphenyl)-5-(4-isopropoxyphenyl)-3-(2,2,3-trimethylbutoxy-1,2,4-triazine,
5,6-bis(4-dimethylaminophenyl)-3-methoxy-1,2,4-triazine,
5,6-bis(4-dimethylaminophenyl)-3-ethoxy-1,2,4-triazine,
5,6-bis(4-dimethylaminophenyl)-3-propoxy-1,2,4-triazine,
5,6-bis(4-dimethylaminophenyl)-3-isopropoxy-1,2,4-triazine,
3-butoxy-5,6-bis(4-dimethylaminophenyl)-1,2,4-triazine,
5,6-bis(4-dimethylaminophenyl)-3-isoheptyloxy-1,2,4-triazine,
5,6-bis(4-diethylaminophenyl)-3-methoxy-1,2,4-triazine,
5,6-bis(4-diethylaminophenyl)-3-ethoxy-1,2,4-triazine,
5,6-bis(4-diethylaminophenyl)-3-propoxy-1,2,4-triazine,
5,6-bis(4-diethylaminophenyl)-3-isopropoxy-1,2,4-triazine,
5,6-bis(4-diethylaminophenyl)-3-pentyloxy-1,2,4-triazine,
5,6-bis(4-dipropylaminophenyl)-3-methoxy-1,2,4-triazine,
3-tert-butoxy-5,6-bis(4-dipropylaminophenyl)-1,2,4-triazine,
5,6-bis(4-dipropylaminophenyl)-3-neoheptyloxy-1,2,4-triazine, 5,6-bis(4-diisopropylaminophenyl)-3-methoxy-1,2,4-triazine,
3-butoxy-5,6-bis(4-diisopropylaminophenyl)-1,2,4-triazine,
5,6-bis(4-diisopropylaminophenyl)-3-(1-ethyl-1-methylpropoxy)-1,2,4-triazine,
5-(4-diisopropylaminophenyl)-6-(4-dimethylaminophenyl)-3-methoxy-1,2,4-triazine,
6-(4-diethylaminophenyl)-3-ethoxy-5-(4-methoxyphenyl)-1,2,4-triazine,
3-benzyloxy-5,6-bis(4-ethoxyphenyl)-1,2,4-triazine,
5,6-bis(4-isopropoxyphenyl)-3-(2-phenylethoxy)-1,2,4-triazine,
5-(4-ethoxyphenyl)-3-(o-methylbenzyloxy)-6-(4-propoxyphenyl)-1,2,4-triazine,
3-benzyloxy-5,6-bis(4-dimethylaminophenyl)-1,2,4-triazine,
5-(4-diethylaminophenyl)-6-(4-diisopropylaminophenyl)-3-(1-phenylethoxy)-1,2,4-triazine,
6-(4-dipropylaminophenyl)-5-(4-methoxyphenyl)-3-(m-methylbenzyloxy-1,2,4-triazine,
3-cycloheptyloxy-5,6-bis(4-ethoxyphenyl)-1,2,4-triazine,
3-cyclobutyloxy-5,6-bis(4-isopropoxyphenyl)-1,2,4-triazine,
3-cyclohexyloxy-5-(4-ethoxyphenyl)-6-(4-propoxyphenyl)-1,2,4-triazine,
5,6-bis(4-diethylaminophenyl)-3-(2-methylcyclopentyloxy)-1,2,4-triazine,
3-cyclobutyloxy-5,6-bis(4-diisopropylaminophenyl)-1,2,4-triazine,
3-cyclohexyloxy-6-(4-diethylaminophenyl)-5-(4-dimethylaminophenyl)-1,2,4-triazine,
5-(4-dipropylaminophenyl)-6-(4-ethoxyphenyl)-3-(2-ethyl-3-methylcyclopentyloxy)-1,2,4-triazine,
5,6-bis(4-methoxyphenyl)-3-(2-methylcyclobutylmethoxy)-1,2,4-triazine,
3-(3-methylcyclopentylmethoxy)-5,6-bis(4-propoxyphenyl)-1,2,4-triazine,
3-cyclohexylmethoxy-5,6-bis(4-dimethylaminophenyl)-1,2,4-triazine,
3-cyclopropylmethoxy-5,6-bis(4-dipropylaminophenyl)-1,2,4-triazine,
5-(4-diethylaminophenyl)-6-(4-dimethylaminophenyl)-3-[2-(2-ethylcyclobutyl)ethoxy]-1,2,4-triazine,
3-(4-cyclopropylbutoxy)-6-(4-dipropylaminophenyl)-5-(4-isopropoxyphenyl)-1,2,4-triazine,
5,6-bis(4-methoxyphenyl)-3-methylthio-1,2,4-triazine,
3-ethylthio-5,6-bis(4-methoxyphenyl)-1,2,4-triazine,
5,6-bis(4-methoxphenyl)-3-propylthio-1,2,4-triazine,
3-isopropylthio-5,6-bis(4-methoxyphenyl)-1,2,4-triazine,
3-butylthio-5,6-bis(4-methoxyphenyl)-1,2,4-triazine,
5,6-bis(4-methoxyphenyl)-3-neoheptylthio-1,2,4-triazine,
5,6-bis(4-ethoxyphenyl)-3-methylthio-1,2,4-triazine,
5,6-bis(4-ethoxyphenyl)-3-ethylthio-1,2,4-triazine,
5,6-bis(4-ethoxyphenyl)-3-propylthio-1,2,4-triazine,
5,6-bis(4-ethoxyphenyl)-3-isopropylthio-1,2,4-triazine,
5,6-bis(4-ethoxyphenyl)-3-(3-methylpentylthio)-1,2,4-triazine,
5,6-bis(4-ethoxyphenyl)-3-octylthio-1,2,4-triazine,
3-methylthio-5,6-bis(4-propoxyphenyl)-1,2,4-triazine,
3-ethylthio-5,6-bis(4-propoxyphenyl)-1,2,4-triazine,
5,6-bis(4-propoxyphenyl)-3-propylthio-1,2,4-triazine,
3-isopropylthio-5,6-bis(4-propoxyphenyl)-1,2,4-triazine,
3-(1,2-dimethylpropylthio)-5,6-bis(4-propoxyphenyl)-1,2,4-triazine,
3-heptyloxy-5,6-bis(4-propoxyphenyl)-1,2,4triazine,
5,6-bis(4-isopropoxyphenyl)-3-methylthio-1,2,4-triazine,
5,6-bis(4-isopropoxyphenyl)-3-pentylthio-1,2,4-triazine,
6-(4-isopropoxyphenyl)-3-methylthio-5-(4-propoxyphenyl)-1,2,4-triazine,
5,6-bis(4-dimethylaminophenyl)-3-methylthio-1,2,4-triazine,
5,6-bis(4-dimethylaminophenyl)-3-ethylthio-1,2,4-triazine,
5,6-bis(4-dimethylaminophenyl)-3-propylthio-1,2,4-triazine,
5,6-bis(4-dimethylaminophenyl)-3-isopropylthio-1,2,4-triazine,
5,6-bis(4-dimethylaminophenyl)-3-isoheptylthio-1,2,4-triazine,
5,6-bis(4-diethylaminophenyl)-3-methylthio-1,2,4-triazine,
5,6-bis(4-diethylaminophenyl)-3-ethylthio-1,2,4-triazine,
5,6-bis(4-diethylaminophenyl)-3-propylthio-1,2,4-triazine,
5,6-bis(4-diethylaminophenyl)-3-isopropylthio-1,2,4-triazine,
5,6-bis(4-diethylaminophenyl)-3-pentylthio-1,2,4-triazine,
5,6-bis(4-diethylaminophenyl)-3-(1,1-dimethylhexylthio)-1,2,4-triazine,
5,6-bis(4-dipropylaminophenyl)-3-ethylthio-1,2,4-triazine,
3-(1,2-dimethylpropylthio)-5,6-bis(4-dipropylaminophenyl)-1,2,4-triazine,
5,6-bis(4-dipropylaminophenyl)-3-(1-ethyl-2-methylbutylthio)-1,2,4-triazine,
5,6-bis(4-diisopropylaminophenyl)-3-ethylthio-1,2,4-triazine,
5,6-bis(4-diisopropylaminophenyl)-3-isobutylthio-1,2,4-triazine,
5,6-bis(4-diisopropylaminophenyl)-3-(2-methylpentylthio)-1,2,4-triazine,
6-(4-diethylaminophenyl)-5-(4-diisopropylaminophenyl)-3-isohexylthio-1,2,4-triazine,
5-(4-dimethylaminophenyl)-6-(4-isopropoxyphenyl)-3-(2-isopropyl-3-methylbutylthio)-1,2,4-triazine,
3-benzylthio-5,6-bis(4-methoxyphenyl)-1,2,4-triazine,
6-(4-isopropoxyphenyl)-5-(4-methyoxyphenyl)-3-(2-phenylethylthio)-1,2,4-triazine,
5,6-bis(4-dipropylaminophenyl)-3-(p-methylbenzylthio)-1,2,4-triazine,
6-(4-diethylaminophenyl)-5-(4-dipropylaminophenyl)-3-(o-methylbenzylthio)-1,2,4-triazine,
3-benzylthio-5-(4-dimethylaminophenyl)-6-(4-methoxyphenyl)-1,2,4-triazine,
3-(2-isopropylcyclopentylthio)-5,6-bis(4-methoxyphenyl)-1,2,4-triazine,
3-(2-ethylcyclobutylthio)-5,6-bis(4-isopropoxyphenyl)-1,2,4-triazine, 3-cyclobutylthio-6-(4-ethoxyphenyl)-5-(4-methoxyphenyl)-1,2,4-triazine,
3-cyclopropylthio-5,6-bis(4-dimethylaminophenyl)-1,2,4-triazine,
5,6-bis(4-diethylaminophenyl)-3-(2-ethylcyclohexylthio)-1,2,4-triazine,
3-cyclopentylthio-5-(4-dimethylaminophenyl)-6-(4-dipropylaminophenyl)-1,2,4-triazine,
6-(4-dipropylaminophenyl)-5-(4-ethoxyphenyl)-3-(2-methylcyclopropylthio)-1,2,4-triazine,
3-(3-methylcyclohexylmethylthio)-5,6-bis(4-methoxyphenyl)-1,2,4-triazine,
3-(2-cyclobutylethylthio)-5,6-bis(4-ethoxyphenyl)-1,2,4-triazine,
3-cycloheptylmethylthio-6-(4-isopropoxyphenyl)-5-(4-propoxyphenyl)-1,2,4-triazine,
3-cyclopropylmethylthio-5,6-bis(4-dimethylaminophenyl)-1,2,4-triazine,
5,6-bis(4-dipropylaminophenyl)-3-[2-(1-methylcyclopentyl)ethylthio]-1,2,4-triazine,
5-(4-diethylaminophenyl)-6-(4-dipropylaminophenyl)-3-(2,3-dimethylcyclopentylmethylthio)-1,2,4-triazine,
3-(2-cyclobutylbutylthio)-6-(4-dimethylaminophenyl)-5-(4-methoxyphenyl)-1,2,4-triazine, and the like, and the pharmaceutically-acceptable acid addition salts of the basic triazines.

The compounds employed in method of the present invention are prepared by a variety of methods known to those having ordinary skill in the art. Starting materials and intermediates also are prepared by known methods. The preparation of 5,6-diaryl-1,2,4-triazines is described generally by J. G. Erickson in "The 1,2,3- and 1,2,4-Triazines, Tetrazines and Pentazines," The Chemistry of Heterocyclic Compounds, Vol. 10, Interscience Publishers, Inc., New York, N.Y., 1956, Chapter II, pp. 44–84. The 5,6-diaryl-1,2,4-triazines which are unsubstituted in the 3-position can be prepared by the catalytic reduction of the corresponding 3-chloro-triazines.

The specific procedure employed to prepare a given 3-substituted-5,6-diaryl-1,2,4-triazine in part is dependent upon the substituent in the 3-position. For example, 3-alkyl-, 3-aralkyl-, 3-cycloalkyl-, and 3-(cycloalkyl)alkyl-5,6-diaryl-1,2,4-triazines can be prepared directly by the cyclization of acylhydrazones of α-diketones by ammonium acetate in hot acetic acid under controlled conditions; see, e.g., C. M. Atkinson and H. D. Cossey, J. chem. Soc., 1962, 1805 [Chem. Abstr., 57:4662l (1962)]. Such triazines also can be prepared from 3-chloro-5,6-diaryl-1,2,4-triazines by the procedure of E. C. Taylor and S. F. Martin [J. Amer. Chem. Soc., 94, 2874 (1972)] which involves the nucleophilic displacement of chlorine by a Wittig reagent which may be generated in situ from an alkyl-, aralkyl-, cycloalkyl-, or (cycloalkyl)alkyltriarylphosphonium halide.

3-chloro-5,6-diaryl-1,2,4-triazines also can be employed to prepare the 3-alkoxy, 3-aralkoxy-, 3-cycloalkoxy-, 3-(cycloalkyl)alkoxy-, 3-alkylthio-, 3-aralkylthio-, 3-cycloalkylthio-, 3-(cycloalkyl)alkylthio-5,6-diaryl-1,2,4-triazines via the nucleophilic displacement of chlorine by the appropriate alcohol or thiol. The 3-alkylthio-, 3-aralkylthio-, 3-cycloalkylthio-, and 3-(cycloalkyl)alkylthio- compounds can be converted to the 3-alkoxy-, 3-aralkoxy-, 3-cycloalkoxy-, and 3-(cycloalkyl)alkoxy-5,6-diaryl-1,2,4-triazines, again via nucleophilic displacement by the appropriate alcohol. The 3-alkylthio-, 3-aralkylthio-, 3-cycloalkylthio-, and 3-(cycloalkyl)alkylthiotriazines in many cases can be prepared by treating the appropriate 3-mercapto-5,6-diaryl-1,2,4-triazine with the appropriate hydrocarbyl halide in the presence of base, particularly when the hydrocarbyl halide is primary or secondary.

3-Chloro-5,6-diaryl-1,2,4-triazines are readily obtained by treating the appropriate 3-hydroxytriazine with phosphorus oxychloride. 3-Hydroxy- and 3-mercapto-5,6-diaryl-1,2,4-triazines in turn can be prepared by condensing an appropriate benzil with semicarbazide or thiosemicarbazide, respectively.

The required benzils are prepared by the oxidation of the corresponding benzoins with copper sulfate in pyridine; see H. T. Clarke and E. E. Driger, Org. Synthesis, Coll. Vol. I, 87 (1941). The benzoins are prepared by the condensation of aromatic aldehydes with cyanide ion; see W. S. Ide and J. S. Buck, Org. Reactions, 4, 269 (1948).

Another approach to the compounds employed to the present invention involves the use of benzils having substituents which can be displaced to give the desired $R_2$ or $R_3$ substituent. For example, the halogen on the phenyl ring at the 5-position in 5-(4-halophenyl)-6-aryl-1,2,4-triazines can be displaced with an alcohol or a dialkylamine to give the corresponding 5-(4-alkoxyphenyl)- or 5-(4-dialkylaminophenyl)- compound, respectively.

The use of two different aromatic aldehydes in the benzoin synthesis leads to unsymmetrical benzils. That is, in a benzil of the formula,

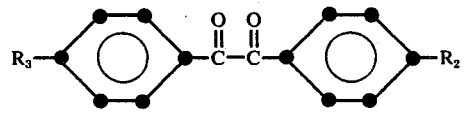

wherein $R_2$ and $R_3$ are as described hereinbefore, $R_2$ and $R_3$ are different. The use of an unsymmetrical benzil may result in the preparation of a mixture of triazine isomers. For example, the condensation of 4-dimethylamino-4'-methoxybenzil with thiosemicarbazide gives a mixture of 5-(4-dimethylaminophenyl)-6-(4-methoxyphenyl)-1,2,4-triazine-3-thiol and 6-(4-dimethylaminophenyl)-5-(4-methoxyphenyl)-1,2,4-triazine-3-thiol.

It will be recognized by those skilled in the art that mixtures of triazine isomers are separable by known methods, such as fractional crystallization and chromatography. The isomer separation may be effected upon intermediate mixtures or delayed until the final product stage.

Certain of the 5,6-diaryl-1,2,4-triazines employed herein are sufficiently basic to form acid addition salts, especially when the triazine contains one or more dialkylamino groups on the phenyl rings. Pharmaceutically-acceptable acid addition salts are well known to those skilled in the art and in general are formed by reacting in a mutual solvent a stoichiometric amount of a suitable acid with a basic triazine. Such salts should not be substantially more toxic to warm-blooded animals than the triazines. While the choice of a salt-forming acid is not critical, in some instances a particular acid may result in a salt having special advantages, such as ready solubility, ease of crystallization, and the like. Representative and suitable acids include, among others, the following: hydrochloric, hydrobromic, hydriodic, sulfuric, nitric, phosphoric, methanesulfonic, p-toluenesulfonic, and the like.

As stated hereinbefore, the present invention provides a method of treating inflammation in a warm-blooded mammal which comprises topically administering to such mammal as effective amount of a compound of the formula,

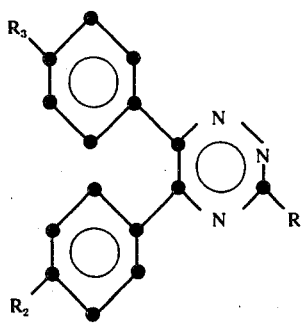

wherein R, $R_2$, and $R_3$ have the meanings previously defined; and the pharmaceutically-acceptable acid addition salts of basic members thereof.

The preferred compounds are those wherein $R_2$ and $R_3$ in the above-defined formula are $C_1$-$C_3$ alkoxy. More preferably, $R_2$ and $R_3$ will be the same, and most preferably are methoxy. With respect to the substituent in the 3-position, the preferred groups are $C_1$-$C_8$ alkyl ( R is $-(X)_nR_1$, n is 0, and $R_1$ is $C_1$-$C_8$ alkyl), $C_1$-$C_8$ alkoxy (R is $-(X)_nR_1$, n is 1, X is O, and $R_1$ is $C_1$-$C_8$ alkyl), and $C_1$-$C_8$ alkylthio (R is $-(X)_nR_1$, n is 1, X is S, and $R_1$ is $C_1$-$C_8$ alkyl). More preferably, the 3-substituent is $C_1$-$C_8$ alkyl or $C_1$-$C_8$ alkoxy. Most preferably, the 3-substituent is $C_1$-$C_3$ alkyl or $C_1$-$C_3$ alkoxy. Illustrative of the compounds which can be employed in the method of the present invention, as well as such preferred, more preferred, and most preferred compounds, are the triazines listed hereinabove.

A modification of the method of Winder was used to measure the anti-inflammatory activities of the compounds employed in the method of the present invention; see C. V. Winder, et al., *Arch. Int. Pharmacodyn.*, 116, 261 (1958). Albino guinea pigs of either sex, weighing 225-300 grams, were shaved on the back and chemically depilated (Nair Lotion Hair Remover, Carter Products, N.Y., N.Y.) 18-20 hours before exposure to ultraviolet light. The animals, in groups of four and bearing identifying ear tags, were treated by applying to an area of skin of about 12 cm.² a solution of test compound dissolved in 0.1 cc. of ethanol. The control treatment consisted of administering only the drug vehicle, ethanol, to a group of four animals. Groups of four animals each given different treatment levels of test compound to obtain dose responses. Random order and blind administration of the test compounds were employed; drug idenfication was not made until after all animals were graded. Immediately prior to drug application, the animals were exposed in groups of four to a high-intensity ultraviolet light for a measured period of time (usually 4-7 seconds). The ultraviolet light source, a Hanovia Lamp (Kroymayer-Model 10), was placed in contact with the skin of the animal's back. A gummed notebook paper reinforcement was affixed to the lamp lens to provide an unexposed area of contrast for grading the erythema. Beginning one hour after exposure and thereafter at half-hour intervals for another 1 ½ hours, the degree of resulting erythema was graded by an arbitrary scoring system based upon the degree of contrast and redness formed. Anti-inflammatory agents delay the development of the erythema and usually have their greatest effect at the initial grading periods. The scores were, therefore, weighted by factors of 4, 3, 2, and 1 at the 1.0, 1.5, 2.0, and 2.5 hour scoring times, respectively. The erythema was graded as follows:

| Erythema Scoring System | |
|---|---|
| Score | Appearance of Exposed Area |
| 0 | No redness and no contrast |
| 1 | Slight redness with a faint reinforcement outline |
| 2 | Slight to moderate redness with a distinct outline |
| 3 | Marked redness with a distinct circular outline |

Total scores from each treatment group of four guinea pigs were prepared to the control treatment, and the percent inhibition was calculated as follows:

$$100 \times \frac{\text{Control Score} - \text{Treatment Score}}{\text{Control Score}} = \text{Percent Inhibition}$$

A dose-response graph was obtained by plotting dose versus percent inhibition, the points representing the average of each treatment group of four guinea pigs. The dose ($ED_{50}$) in micrograms per 12 cm.² (mcg./12 cm.²) which produced a 50% inhibition of the erythemic response for the particular compound tested was obtained in several instances by extrapolation. Table I below summarizes the results obtained from testing representative compounds employed in the invention by the foregoing method. The plotted or calculated $ED_{50}$ for the particular compound tested, where available, is given in the last column of Table I.

Table I

Erythemic response inhibition of 5,6-Diaryl-1,2,4-triazines

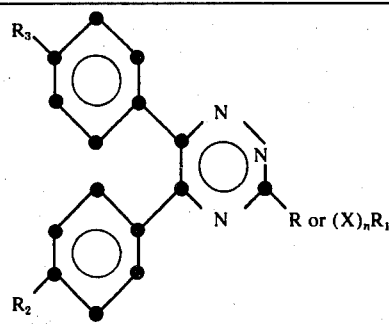

| R or $R_1$ | X | n | $R_2$ | $R_3$ | Inhibition Dose[a] | %[b] | $ED_{50}$[a] |
|---|---|---|---|---|---|---|---|
| H[c] | — | — | —OCH₃ | —OCH₃ | 100 | 53 | — |
| —CH₃[d] | — | 0 | —OCH₃ | —OCH₃ | — | — | 2.4 |
| —C₂H₅[d] | — | 0 | —OCH₃ | —OCH₃ | — | — | 4 |
| —CH₃[d] | O | 1 | —OCH₃ | —OCH₃ | — | — | 7 |
| —C₂H₅[d] | O | 1 | —OCH₃ | —OCH₃ | — | — | 3.1 |
| —CH₃[d] | S | 1 | —OCH₃ | —OCH₃ | — | — | 9 |
| —C₂H₅[d] | S | 1 | —OCH₃ | —OCH₃ | — | — | 21.3 |
| —CH(CH₃)₂[d] | S | 1 | —OCH₃ | —OCH₃ | 100 | 35 | — |
| —C₆H₁₃[d] | S | 1 | —OCH₃ | —OCH₃ | — | — | 37.4 |

Table I-continued
Erythemic response inhibition of 5,6-Diaryl-1,2,4-triazines

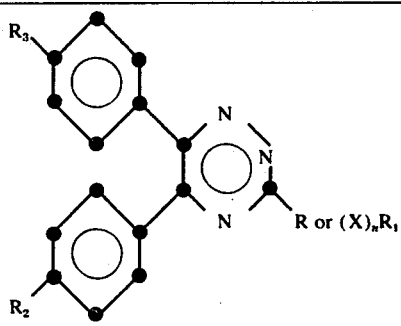

| R or R₁ | X | n | R₂ | R₃ | Inhibition Dose[a] | %[b] | ED₅₀[a] |
|---|---|---|---|---|---|---|---|
| —CH₂C₆H₅[d] | S | 1 | —OCH₃ | —OCH₃ | 100 | 49 | — |

[a] In mcg./12 cm.²
[b] % Inhibition compared with control
[c] R
[d] R₁

The toxicites of representative compounds employed in the method of the present invention, determined as the dose (LD₅₀) in milligrams per kilogram (mg./kg.) of animal body weight which is lethal to 50 percent of mice treated orally, typically are greater than about 1000 mg./kg., and in some cases are greater than about 1500 mg./kg.

The method of the present invention can be used in the treatment of a variety of inflammatory conditions which are susceptible to treatment with topically-active anti-inflammatory agents. Such inflammatory conditions include, among others, atropic determatitis, contact dermatitis, nummular eczema, lichen simplex, psoriasis, chronic dermatoses, and ultraviolet-induced erythema.

In the practice of this invention, one (or more) of the anti-inflammatory triazines is topically administered to a warm-blooded mammal in an effective amount. In general, such amount should be sufficient to provide at least about 1 mcg. of triazine per 12 cm.¹² of skin surface area (1 mcg./12cm.²). Because of the relatively low order of toxicity of such triazines, the maximum level of application basically is limited only by the esthetics of the mode of administration. As a practical matter, however, such triazines normally need not be administered at levels much above about 10³ mcg./12 cm.², although levels of about 10⁵ mcg./12 cm.² or higher can be employed, if desired.

The specific dose level for any given triazine depends upon a number of factors, such as the nature and severity of the inflammatory condition, the potency of the triazine, the concentration of the triazine in the topically applied composition or medicament, the nature of the composition or medicament vehicle, the presence of absorption adjuvants, and the liquid solubility of the triazine. For a discussion of factors involved in the topical absorption of drugs, see "Remington's Pharmaceutical Sciences," 14th Ed., Mack Publishing Company, Easton, Pennsylvania, 1970, pp. 741–746. As already indicated, dose levels can range from about 1 mcg./12 cm.² to about 10⁵ mcg./12 cm.² skin surface area, preferably from about 1 mcg./12 cm.² to about 10³ mcg./12 cm.² The anti-inflammatory triazine can be administered one or more times daily, with multiple applications being preferred. Such multiple applications typically will range from about two to about four per day.

The topical administration of the anti-inflammatory triazines can be made according to any of the well known prior art procedures, which include inunction, spraying, painting, and the like, as well as dispensing from conventional surgical gauze dispensers, collodion, absorbable gelatin film, petrolatum gauze, zinc gelatin, and the like. Thus, such administration can utilize aerosols, creams, emulsions, lotions, oils, ointments, solutions and the like. In each case, the compounds to be employed in accordance with the present invention are utilized in combination with one or more adjuvants suited to the particular mode of application. For example, ointments and the solutions for topical administration can be formulated with any of a number of pharmaceutically-acceptable carriers, including ethanol, animal and vegetable oils, mixtures of waxes, solid and liquid hydrocarbons, glycols, and the like.

Such terms as adjuvants and pharmaceutically-acceptable carriers are meant to include cosmetic carriers and bases, such as ethanol and other organic solvents; oil-in-water and water-in-oil emulsions, employed as both creams and lotions; anhydrous systems, comprising, for example, vegetables waxes, vegetable oils, paraffin waxes, paraffin oils, and any combination thereof; and hydrous gels, utilizing gelatin, xanthate gums, synthetic resins, and the like as gelling agents.

The concentration of the anti-inflammatory triazine in the final topical preparation is not critical. In general, such concentration can range from about 0.001 percent to about 50 percent (w/w or w/v), or higher. Preferably, such concentration will be in the range of from about 0.01 percent to about 10 percent.

If desired, the final topical preparation can contain one or more components having pharmacological or other activities separate and distinct from the activity of the triazines. Examples of such components include, among others, insect repellants, topical anesthetics, bacteriostates, fungicides, astringents, sunscreen agents, and the like. Alternatively, the triazines employed in the method of the present invention can be incorporated into existing or known compositions, such as antiseptics, topical anesthetics, protectives and adsorbents, demulcents, emollients, astrigents, antiphlogistics, antipruritics, and the like, the preparation and use of which are well known to those having ordinary skill in the art; see, for example, "Remington's Pharmaceutical Sciences," supra, pp. 763–786. Of particular preference is the incorporation of such triazines into cosmetic formulations, such as sunscreen, suntan, and sunburn preparations.

In accordance with well known procedures, the final topical preparation can contain, in addition to components already described, solvents, preservatives, emulsifiers, surface active agents, perfumes, water, and the like.

By way of example only, some representative triazine-containing formulations follow. Unless otherwise indicated, all percentages are w/w.

| Ointment | Percent |
|---|---|
| Triazine | 10 |
| Polyethylene glycol 400 (N.F.) | 55 |
| Polyethylene glycol 4000 (U.S.P) | 35 |

| Lotion | Percent |
|---|---|
| Triazine | 1 |
| Ethyl alcohol (denatured) | 69 |
| Oleyl alcohol | 10 |
| Water | 20 |
| Perfume | q.s. |

| Lotion | Percent |
|---|---|
| Triazine | 1 |
| L-43 Silicone[a] | 5 |
| Ethyl alcohol | 94 |
| Perfume | q.s. |

| Oil | Percent |
|---|---|
| Triazine | 2 |
| Castor oil | 90 |
| Butylated hydroxytoluene | 0.02 |
| Ethanol | to 100 |
| Perfume | q.s. |

| Anesthetic ointment | Percent |
|---|---|
| Benzocaine | 5 |
| Triazine | 3 |
| Methylparaben | 0.025 |
| Propylparaben | 0.015 |
| Sodium lauryl sulfate | 1 |
| Propylene glycol | 11 |
| Stearyl alcohol | 24 |
| White petrolatum | 24 |
| Perfume | q.s. |
| Water | to 100 |

| Protective ointment | Percent |
|---|---|
| Zinc oxide | 20 |
| Triazine | 3 |
| Mineral oil | 15 |
| White wax | 3.1 |
| White Petrolatum | 58.9 |
| Perfume | q.s |

| Sunscreen/Insect repellent cream | Percent |
|---|---|
| Triazine | 2 |
| Castor oil | 10 |
| N,N-Diethyltoluamide | 15 |
| Ethyl p-dimethylaminobenzoate | 2 |
| Glyceryl monostearate | 10 |
| Stearic acid | 2 |
| Ethoxylate lanolin alcohol | 2 |
| Butylated hydroxytoluene | 0.02 |
| Cellosize QP 15,000[a] | 0.25 |
| Methylparaben | 0.15 |
| Triethanolamine | 1 |
| Perfume oil | 0.5 v/w |
| Water | to 100 |

| Sunscreen oil | Percent |
|---|---|
| Triazine | 1 |
| Octyl p-dimethylaminobenzoate | 1 |
| Silicone fluid L-45 (100 cS) | 10 |
| Isopropyl palmitate | 88 |

| Aerosol sunscreen oil | Percent |
|---|---|
| Triazine | 1 |
| Ethyl p-dimethylaminobenzoate | 5 |
| Isopropyl myristate | 25 |
| L-43 Silicone[a] | 5 |
| Perfume oil | 1.25 |
| Lanolin oil | 2.5 |
| Menthol Racemic U.S.P. | 0.25 |
| Absolute alcohol | 60 |

| Fill | Percent |
|---|---|
| Concentrate | 20 |
| Propellant 11/12 (75:25)[b] | 80 |

| Palliative preparation for sunburn | Percent |
|---|---|
| Triazine | 5 |
| Colloidal calamine | 10 |
| Triethanolamine stearate | 4.8 |
| Liquid paraffin | 10 |
| Water | 70.2 |
| Antiseptic | q.s. |

| Suntan preparation | Percent |
|---|---|
| Triazine | 1.7 |
| Dihydroxyacetone | 4 |
| Ethanol (95%) | 28 |
| Methyl p-hydroxybenzoate | 1 |
| Sorbitol syrup (70%) | 3 |
| Boric acid powder | 1 |
| Allantoin | 0.3 |
| Distilled water | 59 |
| Perfume | 2 |

[a]Union Carbide Corp., New York
[b]Trichlorofluoromethane/dichlorodifluoromethane The following examples further illustrate the preparations of the compounds employed in the method of the present invention.

EXAMPLE 1

Preparation of 5,6-Bis(4-methoxyphenyl)-3-methyl-1,2,4-triazine (A) 3-Hydroxy-5,6-bis(4-methoxyphenyl)-1,2,4-triazine.

Two moles, 540 g., of anisil (4,4'-dimethoxybenzil), 222 g. (2 moles) of semicarbazide hydrochloride, 180 g. (2.2 moles) of sodium acetate, and 2.5 liters of acetic acid were heated at reflux overnight. The cooled reaction mixture was poured into 5 liters of water. The crude solid product was collected by filtration, washed with water, and recrystallized from acetic acid, giving 434 g. of 3-hydroxy-5,6-bis(4-methoxyphenyl)-1,2,4-triazine, m.p. about 272°–274° C.

Analysis: $C_{17}H_{15}N_3O_3$.

Calc: C, 66.01; H, 4.89; N, 13.58;

Found: C, 65.92; H, 5.04; N, 13.66.

(B) 3-Chloro-5,6-bis(4-methoxyphenyl)-1,2,4-triazine.

Ten grams of 3-hydroxy-5,6-bis(4-methoxyphenyl)-1,2,4-triazine and 50 ml. of phosphorous oxychloride were heated at reflux for 1.5 hours. The cooled mixture was poured onto crushed ice and the resultant mixture was extracted with diethyl ether. The extract was washed successively with 2 percent sodium hydroxide and water until the washings were neutral. The ether extract was dried over anhydrous sodium sulfate and evaporated. The residue was taken up in ether, filtered, and the filtrate was evaporated to yield 9.0 g. of 3-chloro-5,6-bis(4-methoxyphenyl)-1,2,4-triazine, m.p. about 130°–132° C.

Analysis: $C_{17}H_{14}ClN_3O_2$.

C, 63.30; H, 4.31; Cl, 10.82; N, 12.82

Found: C, 62.50; H, 4.48; Cl, 10,53; N, 12.99.

(C) 5,6-Bis(4-methoxyphenyl)-3-methyl-1,2,4-triazine.

To a slurry of 11.7 g. (0.33 mole) of methyltriphenylphosphonium bromide in 150 ml. of dry tetrahydrofuran at −35° C. was added, over a 15-minute period, 20 ml. (0.033 mole) of n-butyl lithium. The reaction mixture was stirred for one hour. To the reaction mixture at −35° to −40° C. was added over a 10-minute period a solution of 5.7 g. (0.0165 mole) of 3-chloro-5,6- bis(4-methoxyphenyl)-1,2,4-triazine in 50 ml. of tetrahydrofuran. The reaction mixture was allowed to warm to ambient temperature and was stirred overnight. A solution of 1.05 g. (0.0165 mole) of sodium carbonate in 50 ml. of water was added dropwise to the reaction mixture which then was heated at reflux for 3 hours. The reaction mixture was cooled, poured over ice, and extracted with diethyl ether. The diethyl ether extract was washed with water, dried over anhydrous sodium sulfate, and concentrated. The concentrate was chromatographed over silica gel, with three fractions being collected. After evaporation of solvent, the third fraction solidified, m.p. about 109°–113° C. The solid was identified as 5,6-bis(4-methoxyphenyl)-3-methyl-1,2,4-triazine by nuclear magnetic resonance analysis, mass spectrographic analysis, and elemental microanalysis.

Analysis: $C_{18}H_{17}N_3O_2$.
Calc: C, 70.34; H, 5.58; N, 13.67;
Found: C, 70.42; H, 5.66; N, 13.33.

EXAMPLE 2

The following compound was prepared by the method of Example 1(C) using the appropriate phosphonium bromide, except that the residue remaining after the evaporation of solvent (diethyl ether) solidified and was recrystallized from petroleum ether/ether acetate:

3-ethyl-5,6-bis(4-methoxyphenyl)-1,2,4-triazine, m.p. about 73°–75.5° C.
Analysis: $C_{19}H_{19}N_3O_2$.
Calc: C, 71.01; H, 5.96; N, 13.08;
Found: C, 71.30; H, 6.01; N, 13.10.

EXAMPLE 3

Preparation of
5,6-Bis(4-methoxyphenyl)-3-methylthio-1,2,4-triazine (A) 3-Mercapto-5,6-bis(4-methoxyphenyl)-1,2,4-triazine.

One hundred grams of anisil (4,4'-dimethoxybenzil) were added to 600 ml. of acetic acid and the mixture was heated to about 100° C. with stirring. Thiosemicarbazide, 68.4 g., was added and the mixture was heated at reflux for about an hour. The mixture was cooled and the solid product was collected by filtration. The solid was washed successively with acetic acid and water. The product was filtered and air dried to yield 96.3 g. of 3-mercapto-5,6-bis(4-methoxyphenyl)-1,2,4-triazine, m.p. about 233°–236° C.
Analysis: $C_{17}H_{15}N_3O_2S$.
Calc: C, 62.75; H, 4.65; N, 12.91; S, 9.85;
Found: C, 62.61; H, 4.57; N, 12.66; S, 9.73.

(B) 3-Methylthio-5,6-bis(4-methoxyphenyl)-1,2,4-triazine.

Eight grams (0.20 mole) of sodium hydroxide were dissolved in 600 ml. of ethanol. The resulting solution was cooled to ambient temperature and 67.0 grams (0.20 mole) of 3-mercapto-5,6-bis(4-methoxyphenyl)-1,2,4-triazine were added. Methyl iodide, 67 g. (0.47 mole), was added to the reaction mixture and the mixture immediately became a slurry. Three hundred milliliters of ethanol were added to the slurry and stirring was continued for about 3 hours. One hundred milliliters of water were added to the reaction mixture and the solid product was collected by filtration. The yield of 5,6-bis(4-methoxyphenyl)-3-methylthio-1,2,4-triazine, m.p. about 152°–155° C., as 67.3 g.

Analysis: $C_{18}H_{17}N_3O_2S$.
Calc: C, 63.70; H, 5.05; N, 12.38;
Found: C, 63.82; H, 5.31; N, 12.10.

EXAMPLES 4–7

The following compounds were prepared by the method of Example 3(B), using the appropriate alkyl halide (given in parenthesis after the compound name):

3-ethylthio-5,6-bis(4-methoxyphenyl)-1,2,4-triazine (from ethyl bromide), m.p. about 118°–120° C., 6.7 g.
Analysis: $C_{19}H_{19}N_3O_2S$.
Calc: C, 64.57; H, 5.42; S, 9.07;
Found: C, 64.78; H, 5.24; S, 9.00.

3-isopropylthio-5,6-bis(4-methoxyphenyl)-1,2,4-triazine (from isopropyl iodide), m.p. about 109°–111° C.
Analysis: $C_{20}H_{21}N_3O_2S$.
Calc: C, 65.37; H, 5.76; S, 8.73
Found: C, 65.65; H, 5.53; S, 8.63.

3-hexylthio-5,6-bis(4-methoxyphenyl)-1,2,4-triazine (from hexyl bromide), m.p. about 92°–94° C., 7 g.
Analysis: $C_{23}H_{27}N_3O_2S$.
Calc: C, 67.45; H, 6.65; S, 7.83; N, 10.26;
Found: C, 67.66; H, 6.71; S, 8.00; N, 10.26.

3-benzylthio-5,6-bis(4-methoxyphenyl)-1,2,4-triazine (from benzyl chloride), m.p. about 128°–130° C., 10.3 g.
Analysis: $C_{24}H_{21}N_3O_2S$.
Calc: C, 69.38; H, 5.09; S, 7.72;
Found: C, 69.37; H, 5.19; S, 7.37.

EXAMPLE 8

Preparation of
3-Methoxy-5,6-bis(4-methoxyphenyl)-1,2,4-triazine (A) Procedure A.

Sodium, 3.0 g. (0.13 mole), was added piecewise under a nitrogen atmosphere to 100 ml. of dry methanol, followed by the addition of a slurry of 31.6 g. (0.1 mole) of 5,6-bis(4-methoxyphenyl)-3-methylthio-1,2,4-triazine in methanol. The reaction mixture was heated at reflux overnight. The reaction mixture was cooled and filtered. The filter cake and the filtrate were extracted with diethyl ether. The diethyl ether was concentrated, giving a solid, m.p. >220° C. The solid was taken up in diethyl ether and the insoluble material was removed by filtration. The filtrate was dried over anhydrous sodium sulfate and concentrated to give a solid residue which was recrystallized from petroleum ether to give 3-methoxy-5,6-bis(4-methoxyphenyl)-1,2,4-triazine, m.p. about 105°–108° C.
Analysis: $C_{18}H_{17}N_3O_3$.
Calc: C, 66.86; H, 5.30; N, 13.00;
Found: C, 67.26; H, 5.97; N, 11.69.

(B) Procedure B.

Sodium, 0.91 g. (0.04 mole), was added piecewise under a nitrogen atmosphere to 100 ml. of dry methanol, followed by the portionwise addition of 11.6 g. (0.036 mole) of 3-chloro-5,6-bis(4-methoxyphenyl)-1,2,4-triazine. The reaction mixture was heated at reflux for three hours, cooled, and stirred overnight. The reaction mixture was cooled and filtered. The filtrate was concentrated and the solid residue was crystallized from petroleum ether/ethyl acetate to give 8.5 g. of 3-methoxy-5,6-bis(4-methoxyphenyl)-1,2,4-triazine, m.p. about 135°–137° C.
Analysis: $C_{18}H_{17}N_3O_3$.
Calc: C, 66.86; H, 5.30; O, 14.86; N, 13.00;

Found: C, 66.84; H, 5.52; O, 14.86; N, 12.79.

EXAMPLE 9

The following compound was prepared by the method of Example 8(B), using ethanol in place of methanol:

3-ethoxy-5,6-bis(4-methoxyphenyl)-1,2,4-triazine, m.p. about 120–122° C., 7.1 g.

Analysis: $C_{19}H_{19}N_3O_3$.

Calc. C, 67.64; H, 5.68; O, 14.23; N, 12.46;
Found: C, 67.92; H, 5.56; O, 14.43; N, 12.38.

EXAMPLE 10

Preparation of
5,6-Bis(4-methoxyphenyl)-1,2,4-triazine

A Parr Low Pressure Hydrogenation Apparatus was charged with 1.5 g. of five percent palladium on charcoal, about 200 ml. of ethyl acetate, 10 g. of 3-chloro-5,6-bis(4-methoxyphenyl)-1,2,4-triazine, and 6 ml. of triethylamine. The apparatus was charged at room temperature with hydrogen and agitated until theoretical hydrogen uptake was obtained. The reaction mixture was filtered and the filtrate was concentrated. The residue solidified and was recrystallized from ethanol to give 6.3 g. of 5,6-bis(4-methoxyphenyl)-1,2,4-triazine, m.p. about 118°–120° C.

Analysis: $C_{17}H_{15}N_3O_2$.

Calc: C, 69.61; H, 5.15; N, 14.33; O, 10.91;
Found: C, 69.37; H, 4.93; N, 14.07; O, 10.99.

What is claimed is:

1. A method of treating inflammation in a warm-blooded mammal which comprises topically administering to such animal an effective amount of a compound of the formula,

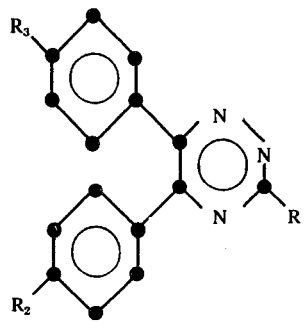

wherein R is hydrogen or $-(X)_nR_1$, in which X is either O or S, n is an integer which is either 0 or 1, and $R_1$ is $C_1$–$C_8$ alkyl, $C_7$–$C_8$ aralkyl, $C_3$–$C_8$ cycloalkyl, or $C_4$–$C_8$ (cycloalkyl)alkyl; and $R_2$ and $R_3$ independently are $C_1$–$C_3$ alkoxy or di($C_1$–$C_3$ alkyl)amino; and a pharmaceutically-acceptable acid addition salt of basic members thereof.

2. The method of claim 1, wherein R is $-(X)_nR_1$, in which $R_1$ is $C_1$–$C_8$ alkyl.
3. The method of claim 2, wherein $R_2$ and $R_3$ both are methoxy.
4. The method of claim 3, wherein $R_1$ is $C_1$–$C_3$ alkyl.
5. The method of claim 4, wherein the compound is 5,6-bis(4-methoxyphenyl)-3-methyl-1,2,4-triazine.
6. The method of claim 4, wherein the compound is 3-ethyl-5,6-bis(4-methoxyphenyl)-1,2,4-triazine.
7. The method of claim 4, wherein the compound is 3-methoxy-5,6-bis(4-methoxyphenyl)-1,2,4-triazine.
8. The method of claim 4, wherein the compound is 3-ethoxy-5,6-bis(4-methoxyphenyl)-1,2,4-triazine.
9. The method of claim 4, wherein the compound is 5,6-bis(4-methoxyphenyl)-3-methylthio-1,2,4-triazine.
10. The method of claim 4, wherein the compound is 3-ethylthio-5,6-bis(4-methoxyphenyl)-1,2,4-triazine.

* * * * *

UNITED STATES PATENT OFFICE
CERTIFICATE OF CORRECTION

Patent No. 4,021,553          Dated May 3, 1977

Inventor(s) William B. Lacefield

It is certified that error appears in the above-identified patent and that said Letters Patent are hereby corrected as shown below:

Column 1, line 59, "timer" should read --time--.

Column 2, line 10, "$C_7 14-C_8$"" should read --$C_7-C_8$--.

Column 2, line 48, "tri-azine." should read --triazine.---.

Column 3, line 20, "(4dipropylaminophenyl)" should read --(4-dipropylaminophenyl)--.

Column 3, line 45, "3-p-" should read --3-(p---.

Column 3, line 61, "4-dipropylamno-", should read --4-dipropylamino---.

Column 4, line 37, "(2-ethylhexyloxy-5" should read --(2-ethylhexyloxy)-5--.

Column 4, line 40, "(2,2,3-trimethylbutoxy-" should read --(2,2,3-trimethylbutoxy)---.

Column 6, line 8, "4triazine" should read --4-triazine--.

Column 6, line 51, "3-isohexylthio)" should read --3-isohexylthio--.

Column 7, line 51, "57:46621" should read --57:4662i--.

Column 7, line 59, "3-chloro" should read --3-Chloro--.

Column 8, line 21, "employed to" should read --employed in--.

Column 9, line 57, "each given" should read --each were given--

Column 11, line 43, "12 cm.$^{12}$" should read --12 cm.$^2$

UNITED STATES PATENT OFFICE
CERTIFICATE OF CORRECTION

Patent No. 4,021,553  Dated May 3, 1977

Inventor(s) William B. Lacefield

It is certified that error appears in the above-identified patent and that said Letters Patent are hereby corrected as shown below:

Column 11, line 58, "liquid" should read --lipid--.
Column 14, line 58, "63.30" should read --62.30--.
Column 15, line 67, "as" should read --was--.

Signed and Sealed this

Eleventh Day of October 1977

[SEAL]

Attest:

RUTH C. MASON
*Attesting Officer*

LUTRELLE F. PARKER
*Acting Commissioner of Patents and Trademarks*